United States Patent [19]

Kneizys et al.

[11] Patent Number: 5,075,856
[45] Date of Patent: Dec. 24, 1991

[54] SYSTEM FOR MODELLING LOW RESOLUTION ATMOSPHERIC PROPAGATION

[75] Inventors: Francis X. Kneizys, Burlington; Eric P. Shettle, Wellesley; Leonard W. Abreu, Chelmsford; James H. Chetwynd, Stoneham; Gail P. Anderson, Concord; William O. Gallery, Winchester, all of Mass.; John E. A. Selby, Huntington, N.Y.; Shepard A. Clough, Lexington, Mass.

[73] Assignee: The United States of America as represented by the Secretary of the Air Force, Washington, D.C.

[21] Appl. No.: 383,372

[22] Filed: Jul. 17, 1989

[51] Int. Cl.$^5$ .................... G06F 15/54; G01J 5/00
[52] U.S. Cl. .................... 364/420; 364/578; 374/121
[58] Field of Search ........... 364/420, 578; 374/121, 374/124

[56] References Cited

U.S. PATENT DOCUMENTS

| | | | |
|---|---|---|---|
| 3,986,002 | 10/1976 | DeMaio | 235/78 R |
| 4,010,357 | 3/1977 | Horner | 364/420 |
| 4,521,861 | 6/1985 | Logan et al. | 364/517 |
| 4,611,929 | 9/1986 | Holyer | 374/124 |
| 4,661,907 | 4/1987 | Arnone et al. | 364/420 |

OTHER PUBLICATIONS

F. X. Kneizys et al., "Atmospheric Transmittance/-Radiance Computer Code LOWTRAN 6", Report No. AFGL-TR-83-0187, dated Aug. 1, 1983, Air Force Geophysics Laboratory (OPI), Hanscom AFB, MA., 01731.

*Primary Examiner*—Clark A. Jablon
*Attorney, Agent, or Firm*—William E. Auton; Donald J. Singer

[57] ABSTRACT

LOWTRAN 7 is a low-resolution propagation model and computer code for predicting atmospheric transmittance and background radiance from 0 to 50,000 cm$^-$ at a resolution of 20 cm$^-$. The code is based on the LOWTRAN 6 (1983) model with a number of improvements. Multiple scattered radiation has been added to the model as well as new molecular band model parameters and new ozone and molecular oxygen absorption parameters for the UV. Other modifications include a wind-dependent desert model, new cirrus cloud models, and new cloud and rain models. The code also includes new representative (geographical and seasonal) atmospheric models and updated aerosol models with options to replace them with user-derived values. An improved extra-terrestrial solar source function is also included. Six modes of program execution are allowed with the new model and computer code for a given slant path geometry.

17 Claims, 5 Drawing Sheets

Microfiche Appendix Included
(399 Microfiche, 9 Pages)

SYSTEM FOR MODELLING LOW RESOLUTION ATMOSPHERIC PROPAGATION

STATEMENT OF GOVERNMENT INTEREST

The invention described herein may be manufactured and used by or for the Government for governmental purposes without the payment of any royalty thereon.

REFERENCE TO MICROFICHE APPENDIX

Reference is made to the microfiche appendix which contains 9 sheets and 399 frames of the LOWTRAN 7 source code.

BACKGROUND OF THE INVENTION

The present invention relates generally to systems which calculate the effects of the atmosphere on the transmission of radio and optical beams, and more specifically to a low resolution propagation model and system for predicting atmospheric transmittance and background radiance from 0 to 50,000 cm$^{-1}$ at a resolution of 20 cm$^{-1}$.

The interest in atmospheric transmittance and background radiance along with the associated subject of astronomical refraction goes back to Laplace. With the advent of large telescopes and phased array radar systems, this interest has become ubiquitous, since the output signals of these systems experience attenuation due to atmospheric particles, water vapor and other gases along the viewing path.

The transmittance and radiance along a path through the atmosphere depend upon the total amount and the distribution of the absorbing or scattering species as well as the variation of pressure and temperature along the path. The integrated amount of absorber or scatterer along a path is known by various names, including "column density", "equivalent absorber amount", and "air mass". While the term "air mass" applies specifically to the total amount of gas along the path, it will be used here to refer loosely to the integrated amounts for all the different species relative to the amount for a vertical path.

The task of ascertaining atmospheric transmittance and atmospheric background radiance is alleviated, to some extent by the systems disclosed in the following U.S Patents, the disclosures of which are incorporated herein by reference:

U.S. Pat. No. 4,611,929 issued to Ronald J. Holyer;
U.S. Pat. No. 4,521,861 issued to Russell H. Logan et al;
U.S. Pat. No. 4,661,907 issued to Robert A. Arnone;
U.S. Pat. No. 4,010,357 issued to Joseph L. Horner; and
U.S. Pat. No. 3,986,002 issued to Dorian A. DeMaio.

Perhaps the most significant of the above-cited references is the Holyer patent. The Holyer reference discloses a satellite method for measuring sea surface temperature which utilizes LOWTRAN 5, which is a predecessor of the present invention.

In February of 1980, the Air Force Geophysics Laboratory of Hanscom Air Force Base, Massachusetts developed LOWTRAN 5, a Fortran computer code designed to calculate atmospheric transmittance and radiance for a given atmospheric path at low spectral resolution. The details of LOWTRAN 5 are described in a technical report by F. Kneizys et al entitled "Atmospheric Transmittance/Radiance; Computer Code LOWTRAN 5, AFGL-TR-80-0067," the disclosure of which is incorporated herein by reference. This report is available from the National Technical Information Service where it is identified as document number ADA088215.

In LOWTRAN 5, 6 and 7, the atmosphere is modeled as a set of spherically symmetric shells with discrete boundaries. The temperature, pressure, and absorber (gas and aerosol) densities are specified at the layer boundaries. Between boundaries, the temperature profile is assumed linear while the pressure and densities are assumed to follow exponential profiles.

LOWTRAN 6 was developed and described in August 1983 in a technical report entitled "Atmospheric Transmittance/Radiance; Computer Code LOWTRAN 6, AFGL-TR-83-0187", the disclosure of which is incorporated herein by reference. This report is available from the National Technical Information Service, where it is identified as document number ADA137796.

LOWTRAN 6 was an improvement over the previous model LOWTRAN 5, which assumed that the index of refraction was constant between layer boundaries. LOWTRAN 6 assumes a continuous profile for the refractive index, with an exponential profile between layer boundaries. It is more accurate than the previous models and works for all paths.

The LOWTRAN 7 model and computer code calculates atmospheric transmittance and background radiance for a given atmospheric path at low spectral resolution. This version is an extension and update of the current code, LOWTRAN 6 (and its predecessors LOWTRAN 5, LOWTRAN 4, LOWTRAN 3 and LOWTRAN 2). All the options and capabilities of the LOWTRAN 6 code have been retained, but additional refinements have been added, as described below.

The LOWTRAN 7 code calculates atmospheric transmittance, atmospheric background radiance, single scattered solar and lunar radiance, direct solar irradiance, and multiple scattered solar and thermal radiance. The spectral resolution of the model is 20 cm$^{-1}$ (full width at half-maximum) in steps of 5 cm$^{-1}$ from 0 to 50,000 cm$^{-1}$ (0.2 um to infinity). A single-parameter band model is used for molecular line absorption and the effects of molecular continuum-type absorption; molecular scattering, aerosol and hydrometeor absorption and scattering are included. Refraction and earth curvature are considered in the calculation of the atmospheric slant path and attenuation amounts along the path. Representative atmospheric, aerosol, cloud, and rain models are provided in the code with options to replace them with user-provided theoretical or measured values.

In view of the foregoing discussion, it is apparent that there remains an ongoing need to obtain refined estimates of atmospheric transmittance and background radiance, and that state-of-the-art methods are literally adapted for use almost as fast as they are developed by users that include the United States Air Force and other DOD agencies. The present invention is intended to satisfy that need.

SUMMARY OF THE INVENTION

LOWTRAN 7 is a low-resolution propagation model and computer system for predicting atmospheric transmittance and background radiance from 0 to 50,000 cm$^{-1}$ at a resolution of 20 cm$^{-1}$. The code is based on the LOWTRAN 6 (1983) model, but has a number of improvements. Multiple scattered radiation has been added to the model as well as new molecular band model parameters and new ozone and molecular oxygen absorption parameters for the UV. Other modifications include a wind-dependent desert model, new cirrus cloud models, and new cloud and rain models. The code also includes new representative (geographical and seasonal) atmospheric models and updated aerosol models with options to replace them with user-derived values. An improved extra-terrestrial solar source function is also included. Six modes of program execution are allowed with the new model and computer code for a given slant path geometry.

The present invention includes a new model for calculating air mass and presents calculations of air mass for several representative atmospheric paths. For a more complete description of the principles behind the method used in both LOWTRAN 6 and LOWTRAN 7, see the technical report by Gallery, W. O. Kneizys, F. X., and Clough, S. A. entitled, "Air Mass Computer Program for Atmospheric Transmittance Radiance/-Calculations: FSCATM," AFGL-TR-83-0065, the disclosure of which is incorporated herein by reference.

The software and instructions for the LOWTRAN 7 package are available from:
National Climatic Data Center, NOAA,
Environmental Data Services,
Federal Building,
Asheville, N.C. 28801,
(704) 259-0272.

There are several techniques available to the user to reduce the executable field length of a program. On CDC CYBER systems, the program may be run using the SEGMENT loader, which effectively creates an overlay structure. LOWTRAN 7 is useable on almost all data processor systems which are capable of operating with FORTRAN (i.e. most FORTRAN 77 compilers) and determines: atmospheric transmittance, atmospheric background radiance, single scattered solar and lunar radiance, direct solar radiance, and multiple scattered solar and thermal radiance. It may be used with external sensor systems which provide either known meteorological atmospheric data (temperature, pressure and density, etc.) or may use one of six internal reference atmospheric models to estimate these conditions as a function of altitude.

In operation LOWTRAN 7 may rely on physical sensors to provide weather data as input in a determination of atmospheric transmittance and background radiance to an infrared system, or a system analogous to the U.S. Navy's satellite temperature measurement system of the above-cited Holyer patent.

It is a principal object of the present invention to provide a low-resolution propagation model for predicting atmospheric transmittance and background radiance to users of systems that include uv visible or infrared tracking systems, communication systems, and satellite weather sensing systems.

It is another object of the present invention to provide a refined estimate of transmittance and multiple scattered radiation using an atmospheric data base that includes molecular profiles for thirteen minor and trace gases, and six reference atmospheric models that define temperature, pressure and density, as a function of altitude, and a number of models for the atmospheric aerosols, clouds and rain.

It is another object of the present invention to calculate the effects of weather on the transmission of infrared and optical beams.

These objects together with other objects, features and advantages of the invention will become more readily apparent from the following detailed description when taken in conjunction with the accompanying drawings wherein like elements are given like reference materials throughout.

DETAILED DESCRIPTION OF THE PREFERRED EMBODIMENT

The present invention includes a low-resolution propagation model and system for predicting atmospheric transmittance background radiance, single scattered solar and lunar radiance, direct solar or lunar irradiance, and multiple scattered solar and thermal radiance. The spectral resolution of the model is 20 cm$^{-1}$ (full width at half-maximum) in steps of 5 cm$^{-1}$ from 0 to 50,000 cm$^{-1}$ (0.2 um to infinity). A single-parameter band model is used for molecular line absorption and the effects of molecular continuum-type absorption; molecular scattering, aerosol and hydrometeor absorption and scattering are included. Refraction and earth curvature are considered in the calculation of the atmospheric slant path and attenuation amounts along the path. Representative atmospheric, aerosol, cloud, and rain models are provided in the code with options to replace them with user-provided theoretical or measured values.

A new atmospheric data base consisting of separate molecular profiles (0 to 100 km) for thirteen (13) minor and trace gases is provided for use with the LOWTRAN 7 model. Six reference atmospheres, each defining temperature, pressure, and density as a function of altitude are included in the program.

As mentioned above, the software and instructions for the LOWTRAN 7 package are available from:
National Climatic Data Center, NOAA,
Environmental Data Services,
Federal Building,
Nasheville, N.C. 28801
(704)259-0272

The description that follows shows how the invention may be used to benefit existing sensor and communication systems.

Figure 1:
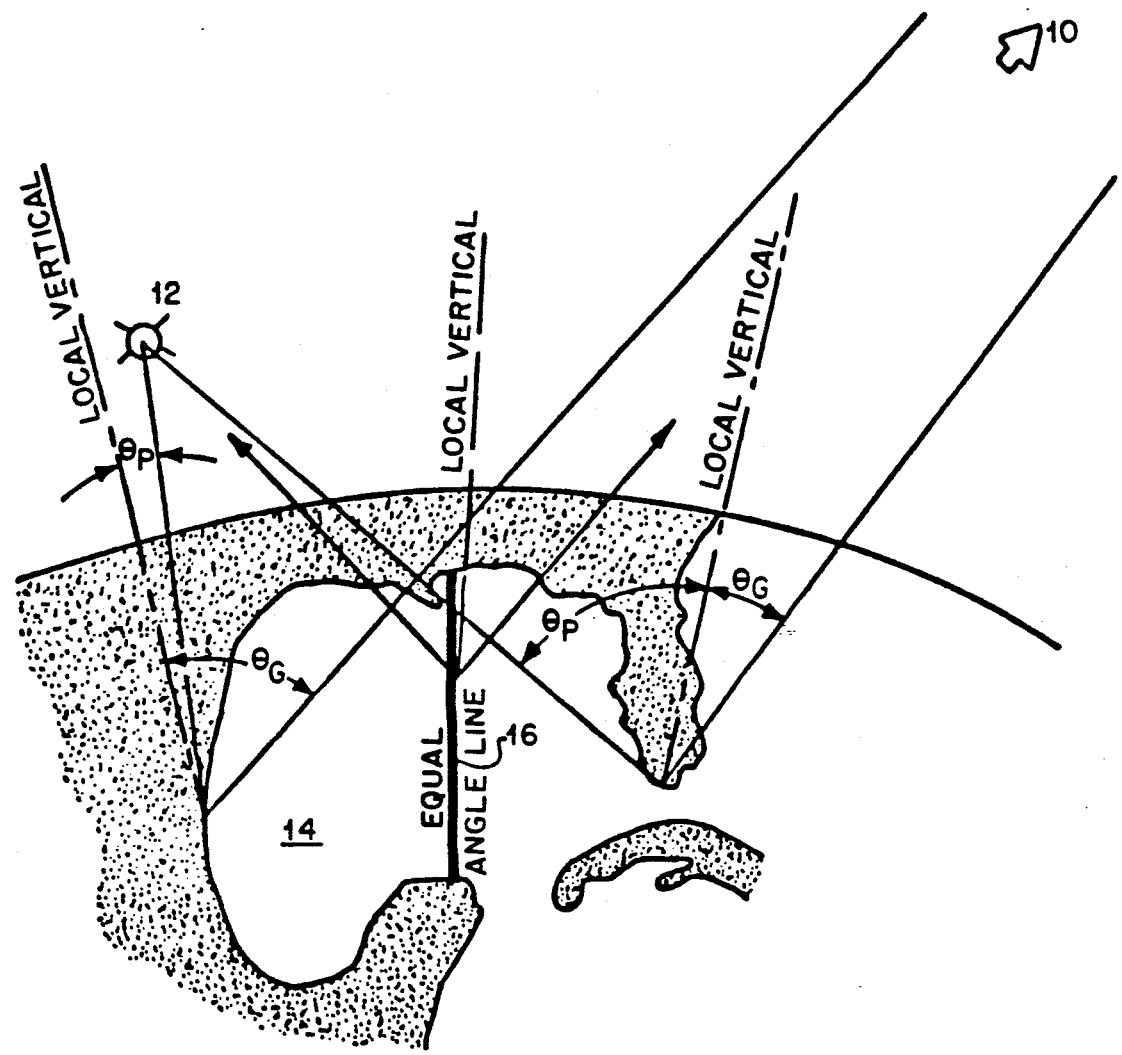
FIG. 1 is an illustration of a prior art host system which can be used with the present invention.

The reader's attention is now directed towards FIG. 1, which is an illustration of a satellite system used by the U.S. Navy to measure sea surface temperature which relies on LOWTRAN 5 (a predecessor of the present invention). The system of FIG. 1 is presented in order to demonstrate a practical application of the present invention with an external sensor system.

The system of FIG. 1 uses a geostationary satellite 10 and a polar orbiting satellite 12 to acquire infrared imagery of an oceanographic study area 14. The sensors aboard the geostationary satellite 10 and the polar orbiting satellite 12 observe the same apparent sea surface temperature values along the equal angle line 16 since both satellites are looking at the same point on the ocean surface through the same atmospheric path length. If the observed temperatures along the equal angle line 16, are not equal, the significant factor is calibration differences between the two sensors. The calibration errors are eliminated by adjusting the calibration curve of one satellite so that the temperatures along the equal angle line 16 match the temperatures of the other satellite, i.e., the satellite which is considered to be better calibrated.

The system of FIG. 1 is able to refine its estimate of the sea surface temperature through the use of LOWTRAN 5, and could also make use of the present invention as an atmospheric model. Both LOWTRAN 5 and LOWTRAN 7 are atmospheric models for predicting atmospheric transmittance and background radiance. The significance of such a model on sensor systems such as the one in the above-cited Holyer reference is described in the paragraphs that follow.

The absorption and emission of infrared radiative energy in the atmosphere is due mainly to vibrational and rotational energy bands of the triatomic molecules: water vapor, carbon dioxide and ozone. The LOWTRAN program has the option to calculate atmospheric and earth radiance. A numerical evaluation of the integral form of the equation of radiative transfer is used in the program. The emission from aerosols and the treatment of aerosol and molecular scattering is considered only in the zeroth order. Additional contributions to atmospheric emission from radiation scattered one or more times are neglected. Local thermodynamic equilibrium is assumed in the atmosphere.

The average atmospheric radiance (over a 20 cm$^{-1}$ interval) at the wavenumber, v, along a given line-of-sight in terms of the LOWTRAN transmittance parameters is given by $$I(v) = \int_{\tau_a^b}^{1} d\tau_a B(v, T)\tau_s + B(v, T_b)\tau_t^b \quad (1)$$

where the integral represents the atmospheric contribution and the second term is the contribution of the boundary, (for example, the surface of the earth or a cloud top) and $\tau_a$ = average transmittance due to absorption,
$\tau_s$ = average transmittance due to scattering,
$\tau_t = \tau_a \tau_s$ = average total transmittance,
$\tau_a^b$, $\tau_t^b$ = average total transmittances from the observer to boundary, $B(v,T)$ = average Planck (blackbody) function corresponding to the frequency v and the temperature T of an atmospheric layer.

$T_b$ = temperature of the boundary.

The emissivity of the boundary is assumed to be unity.

The LOWTRAN band model approach used here assumes that since the blackbody function is a slowly varying function of frequency we can represent the average value of the radiance in terms of the average values of the transmittance and the blackbody function. $\tau_a$, $\tau_s$, and $\tau_t$ vary from 1 to $\tau_a^b$, $\tau_s^b$, and $\tau_t^b$ along the observer's line-of-sight. For lines of sight which do not intersect the earth or a cloud layer, the second term in Eq. (1) is omitted.

The numerical analogue to Eq. (1) has been incorporated in the LOWTRAN computer program. The numberical integration of the radiance along a line-of-sight for a given model atmosphere defined at N levels is given by $$I(v) = \sum_{i=1}^{N-1} (\tau_a(i) - \tau_a(i+1))B\left(v, \frac{T(i) + T(i+1)}{2}\right)\left(\frac{\tau_s(i) + \tau_s(i+1)}{2}\right) +$$

Thus, the spectral radiance from a given atmospheric slant path (line-of-sight) can be calculated by dividing the atmosphere into a series of isothermal layers and summing the radiance contributions from each of the layers slong the line-of-sight, that is, numerically evaluating Eq. (1). This is provided in the atmospheric model of LOWTRAN 7.

LOWTRAN 7 has a number of differences that distinguish it from its predecessors. For example, separate band models and band model absorption parameters are included in the LOWTRAN 7 model and code for the following molecules: $H_2O$, $O_3$, $N_2O$, $CH_4$, $CO$, $O_2$, $CO_2$, $NO$, $NO_2$, $NH_3$, and $SO_2$. Analytic transmission functions (double-exponential) replace numerical tables used in previous LOWTRAN models. The new models were developed with and based on degraded line-by-line spectra and validated with laboratory measurements. (See Pierlnissiard Moragauchkis/AFGL-TR-86-0272)

A modification was made in the water vapor continuum absorption near 10 um from that of LOWTRAN 6. The self density dependent continuum absorption values in this region were reduced approximately twenty percent based on laboratory measurements and the atmospheric measurements.

New ultraviolet absorption parameters for molecular oxygen (Schumann-Runge bands, Herzberg continuum) have been added to the code. The absorption data for ozone in this region (Hartley and Huggins bands) has been updated or improved based on more recent data including the addition of temperature dependent absorption coefficients.

An improved extra-terrestrial solar source function is included in the LOWTRAN 7 model. The data for this function are based on the work of Van Hoosier et al, Neckel & Labs Werhli, and Thekeakara. It covers the spectral region from 0 to 57,470 cm$^{-1}$ and is generally compatible with the resolution of the molecular absorption parameters of the LOWTRAN model.

An efficient and accurate multiple scattering parameterization has been implemented in the LOWTRAN model based on the two stream approximation and an adding method for combining atmospheric layers. An interface scheme was also developed using the l.c.-distribution method to match the multiple scattering approach to the LOWTRAN band model calculation of molecular gaseous absorption. The error of the multiple scattering parameterization in solar and thermal radiance calculations considering all possible viewing angles is estimated to be less than twenty percent. (See Isaacs et al, AFGL-TR-86-0073)

For LOWTRAN 7, all the existing aerosol models and the rain model in the previous LOWTRAN 6 model were extended through the millimeter wavelength region. In addition, the Navy Maritime model was modified to improve its wind speed dependence for the large particle component. Water cloud models (cumulus, stratus, altostratus, strato-stratocumulus and nimbostratus) from FASCOD2 has also been added. The new cirrus cloud models with a realistic wavelength dependence and separate absorption, scattering and asymmetry parameters were developed for LOWTRAN 7 as well as a new aerosol model for desert conditions with a wind speed dependence. The program now provides for modified aerosol profiles over elevated surfaces.

For the stratospheric aerosols additional combinations of the wavelength dependent extinction coefficient models (background stratospheric, aged volcanic or fresh volcanic) and the vertical distribution profiles (background and moderate, high or extreme volcanic), are available. The background stratospheric extinction model has been modified to utilize new refractive index data and size distribution measurements.

Figure 2:
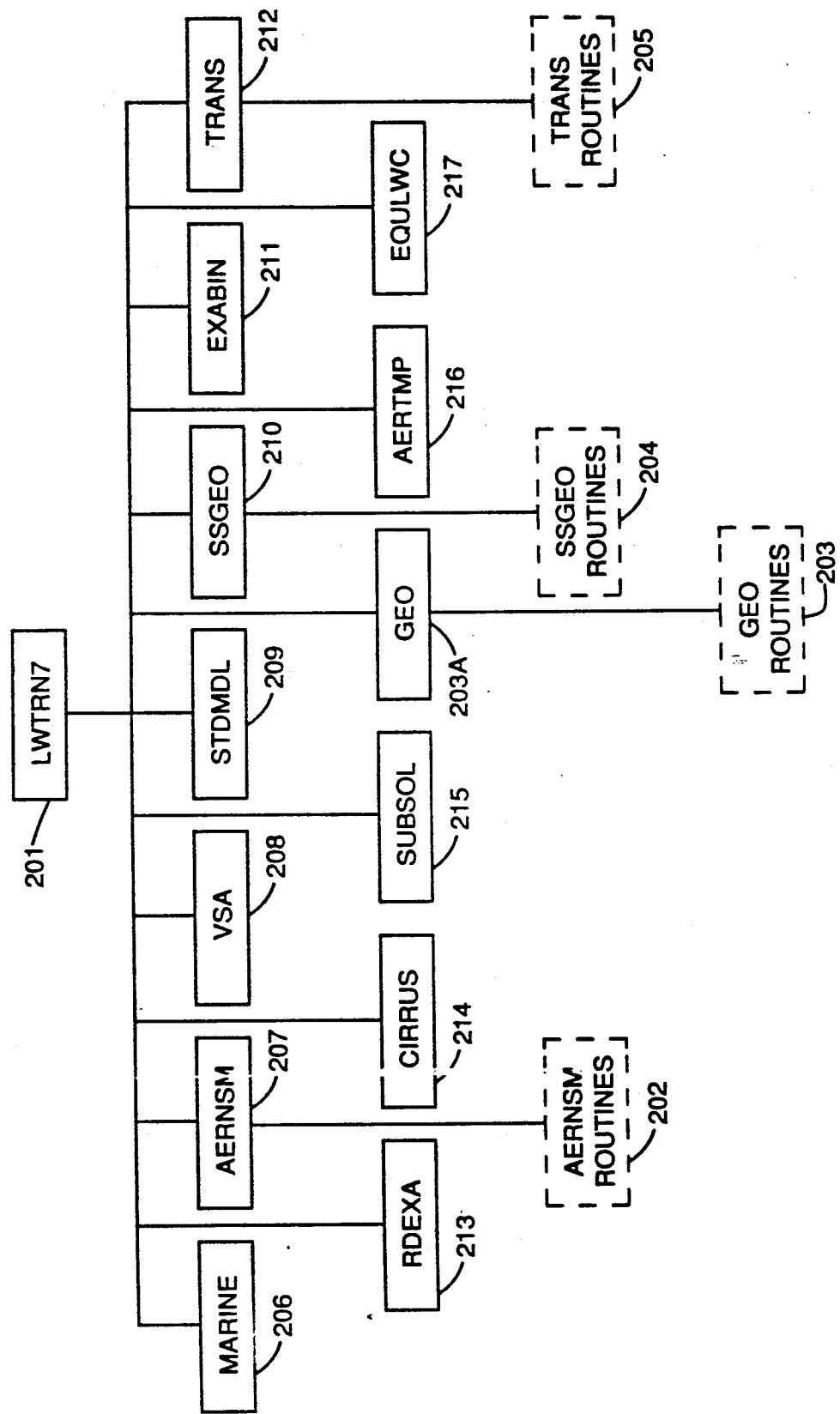
FIG. 2 is a block diagram of the main program structure of LOWTRAN 7.

The reader's attention is now directed towards FIG. 2, which is a block diagram of the main program LOWTRAN 7. This figure indicates that LOWTRAN 7 is composed of a total of seventeen modules of subroutines 201-217, which are identified below in table 1, and described in further detail below.

The first subroutine 201 is the main driver program. This program reads the control cards input into the FORTRAN computer by the user, and initiates all other subroutines as directed by the user.

The MARINE subroutine 206 determines aerosol extinction and absorption coefficients the boxes enclosed by dashes are modules of subroutines for the calculations of non-standard models, air mass geometry, single scattering geometry and transmittance. The first of these AERNSM 207, defines a model atmosphere, aerosol profile and cloud profile. The characteristics of the model atmosphere of the AERNSM subroutine are defined below in Table 2.

The GEO subroutine 203 is a set of air mass subroutine which calculates attenuator amounts for a particular slant path selected by the user. The SSGEO subroutine 204 obtains attenuator amounts from scattering points along a chosen optical path to an extraterrestrial source.

The TRANS set of subroutines 205 calculates transmittance, atmospheric radiance, and solar/lunar scattered radiance for a slant path. It also evaluates vertical profiles of optical quantities required for multiple scattering calculations.

The VSA subroutine 208 is a vertical structure algorithm of aerosol extinction and relative humidity for low visibility and low ceiling conditions. The subroutine labeled STDMDL 208 sets up scaled densities from the model atmosphere. The GEO routine 203 is the driver for the air mass subroutines and calculates attenuator amounts for a selected slant path.

The AERTMP subroutine 216 defines a temperature for each aerosol altitude region and the EQULWC subroutine 217 calculates the liquid water content of standard aerosols.

TABLE 1

| | Description of LOWTRAN 7 Subroutines |
|---|---|
| LWTRN7 | Main driver program. Reads control cards. |
| MARINE | Determines aerosol extinction and absorption coefficients for the Navy maritime model. |
| RDNSM | Reads user input data when model 7 and VSA option are selected. |
| JOU | Interpretive routine for JCHAR |
| CHECK | Units conversion for pressure and temperature |
| DEFALT | Chooses a stored atmospheric profile and interpolates default values for a specific altitude |
| CONVRT | Accommodates uniform data input for model 0 or 7 |
| WATVP | Computes water vapor number density (mol cm$^{-3}$) to accommodate "JCHAR" definitions for uniform data input |
| RDEXA | IHAZE 7 or ICLD 11 triggers up to 4 regions of user input |
| AERNSM | Defines model atmosphere, aerosol profile and cloud profile |
| CIRRUS | Generates altitude profiles of cirrus cloud density. |
| RANDOM | Calls machine-dependent function RANF, that is a uniform random number generator. |
| VSA | Army vertical structure algorithm of aerosol extinction and relative humidity for low visability/low ceiling conditions |
| SUBSOL | Calculates the subsolar point angles based upon time and day. |
| STDMDL | Sets up scaled densities from the model atmosphere |
| GEO | Driver for air mass subroutines. Calculates attenuator amounts for the slant path. (GEO can be called by both SSGEO and in the main driver) |
| AERTMP | Defines temperature for each aerosol altitude region |
| SSGEO | Obtains attenuator amounts from scattering points along optical path to the extraterrestrial source. |
| EXABIN | Loads aerosol extinction, absorption and scattering. |
| EQULWC | Calculates liquid water content of standard aerosols |
| TRANS | Calculates transmittance, atmospheric radiance, and solar/lunar scattered radiance for slant path. Sets up data for double exponential band model. Evaluates vertical profiles of optical quantities required for multiple scattering calculations. |

Tables 2-6 respectively describe the AERNSM, AIR MASS, SSGEO and TRANS subroutines depicted in FIG. 2. FIGS. 3-6 are charts which respectively depict; the single and multiple scattered solar radiance function used in FIG. 2; the radiance and multiple scattered radiance function used in FIG. 2; the atmosphere transmittance function of FIG. 2; and the solar irradiance function of FIG. 2. These functions are described briefly below.

Figure 3:
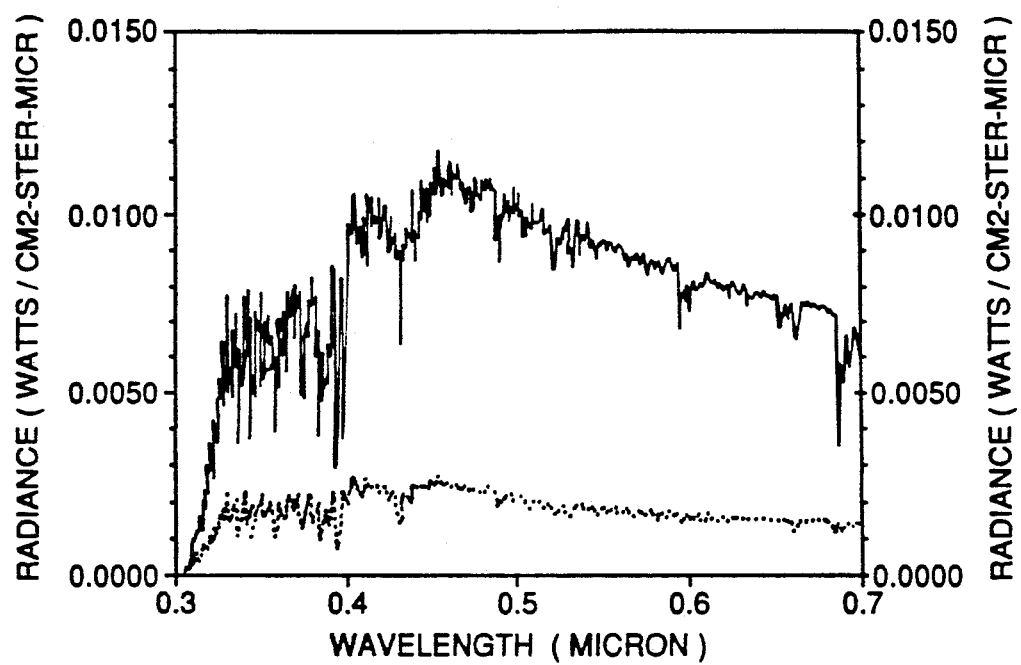
FIG. 3 is a chart of the single and multiple scattered solar radiance relationships used in the present invention.

FIG. 3 is a chart which represents the single and multiple scattered, solar radiance. The path for this case is from 20 km to 0 km, and the solar zenith angle is 60°. The solid line is the multiple scattered radiance and the dotted line shows the contribution due to single scattered solar radiance.

Figure 4:
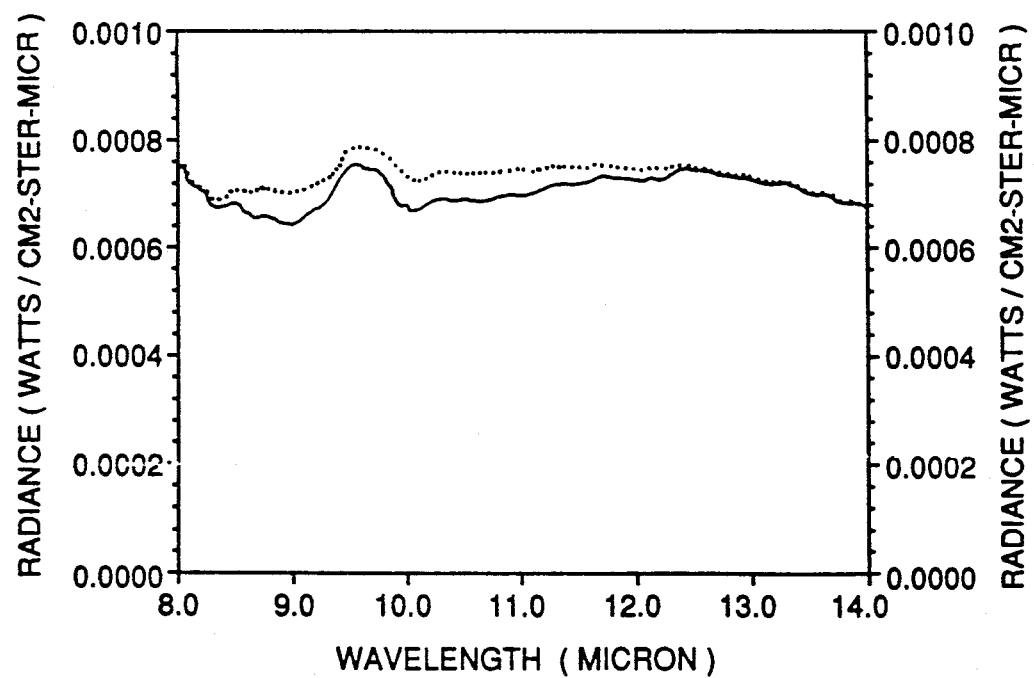
FIG. 4 is a chart which represents the thermal radiance and the multiple scattered radiance relationships used in the present invention.

FIG. 4 is a chart which represents the multiple scattered radiance and a straight forward radiance calculation for conservative scattering. This is a slant path to space (0 to 100 km) The solid line is the result due to multiple scattering and the dotted line is the result of a radiance calculation.

Figure 5:
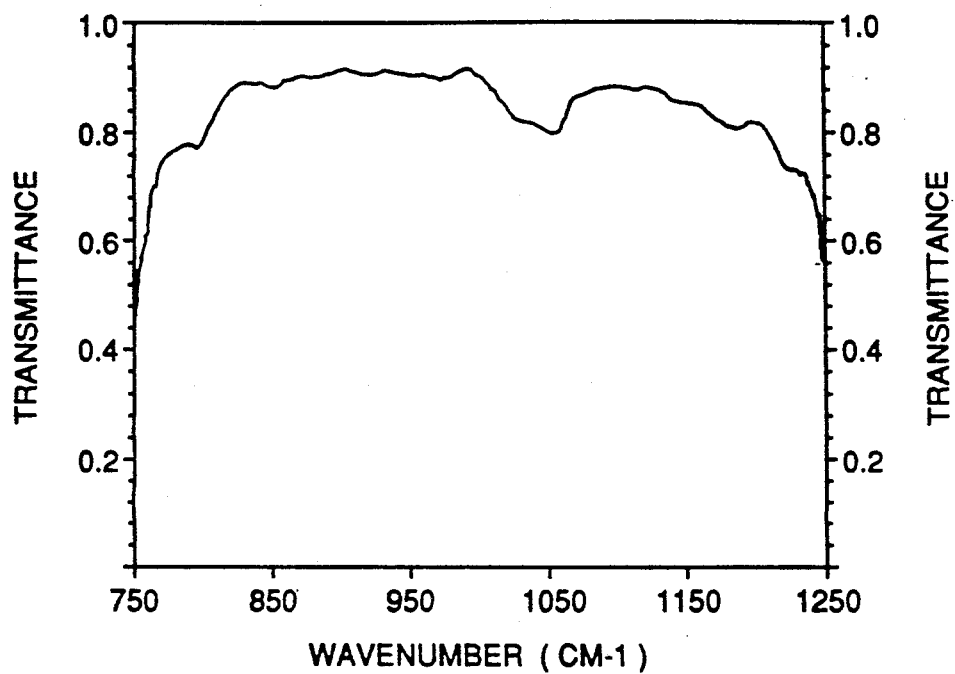
FIG. 5 is a chart which represents the atmospheric transmittance relationship used in the present invention.

FIG. 5 is a chart which represents the atmospheric transmittance with an elevated surface of 1.5 km. The path is from 1.5 to 6 km looking straight up.

Figure 6:
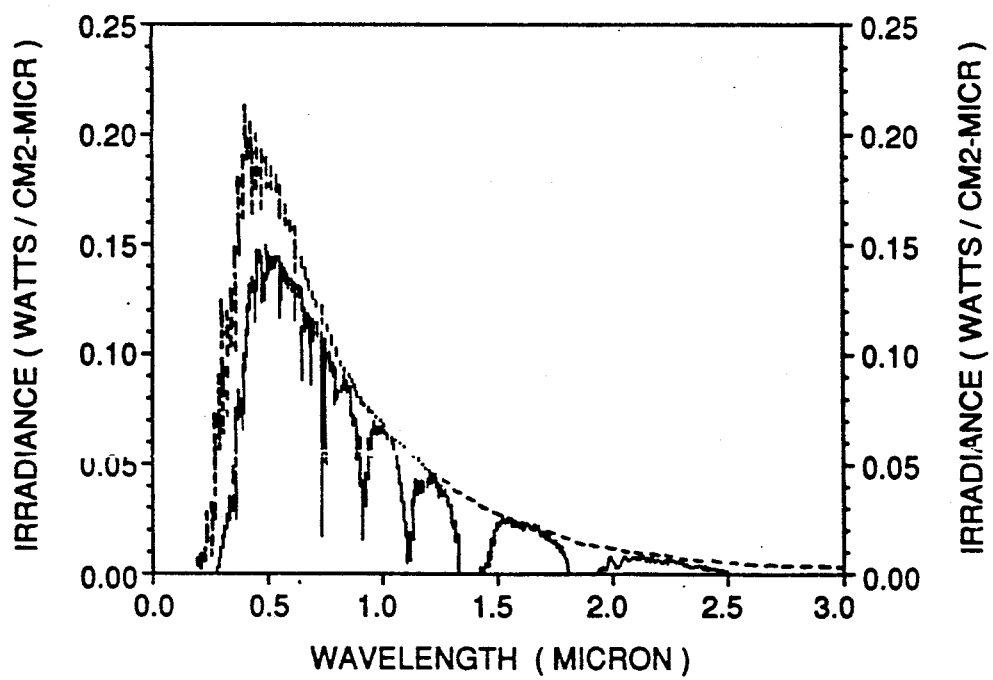
FIG. 6 is a chart which represents the directly transmitted solar radiance relationship used in the present invention.

FIG. 6 is a chart which represents the directly transmitted solar irradiance. The path is from ground to space with an angle of 0°. The solid line is the directly transmitted solar irradiance and the dashed line is the solar radiance.

TABLE 2

Description of AERNSM Subroutines

| | |
|---|---|
| AERNSM | Defines model atmosphere, aerosol profile and cloud profiles. |
| CIRR18 | New thick cirrus profile and new optically thin cirrus profile |
| FLAYZ | Final LOWTRAN altitude boundaries |
| JOU | Interpretive routine for JCHAR |
| CHECK | Units conversion for Pressure and Temperature |
| DEFALT | Chooses a stored atmospheric profile and interpolates default values for a specific altitude |
| CONVRT | Accommodates uniform data input for MODEL 0 or 7 |
| WATVAP | Computes water vapor number density (mol cm$^{-3}$) to accommodate "JHAR" definitions for uniform data input |
| VSANSM | Used with VSA and MODEL 7 |
| LAYVSA | layering of atmosphere with VSA model |
| LAYCLD | layering of atmosphere with ICLD 1 to 11 |
| MARINE | Determines aerosol extinction and absorption coefficients for the Navy maritime model |
| DESATT | Determines aerosol extinction and absorption coefficients aerosol profiles for desert model |
| CLDPRF | Standard cloud profiles |
| AERPRF | Computer density profiles for aerosols |

TABLE 3

Description of Air Mass Subroutines

| | |
|---|---|
| GEO | Driver for air mass subroutines, Calculates attenuator amounts for the slant path. |
| GEOINP | Interprets geometry input parameters into the standard form H1, H2, ANGLE, and LEN. |
| FNDHMN | Calculates HMIN, the minimum altitude along the path and PHI, the zenith angle at H2. |
| REDUCE | Eliminates slant path segments that extend beyond the highest profile altitude. |
| FDBETA | Calculates angle, given H1, H2 and BETA by iteration |
| RFPATH | Determines the refracted path and the absorber amounts through all the layers. |
| FILL | Defines the boundaries of the slant path and interpolates densities at these boundaries. |
| LAYER | Calculates the path and amounts through one layer. |
| RADREF | Computes radius of curvature of the refracted ray for a horizontal path. |
| FINDSH | Finds layer boundaries and scale height at ground for index of refraction. |
| SCALHT | Calculates scale height of index of refraction. |
| ANDEX | Computes index of refraction at a specific height. |
| EXPINT | Performs exponential interpolations for the geometry routines. |

TABLE 4

Description of SSGEO Subroutines

| | |
|---|---|
| SSGEO | Obtains attenuator amounts from scattering points along optical path to the extraterrestrial source. |
| PSIDEL | Calculates the relative azimuth between the line of sight and the direct solar/lunar path. |
| PSI | Returns solar azimuth relative to line-of-sight at current scattering location. |
| DEL | Returns solar zenith angle at any point along optical path. |
| GEO | Driver for air mass subroutines. Calculates attenuator amounts for the slant path. |
| SCTANG | Returns the scattering angle at any point along the optical path. |

TABLE 5

Description of TRANS Subroutines

| | |
|---|---|
| TRANS | Calculates transmittance, atmospheric radiance, and solar/lunar scattered radiance for slant path. Sets up data for double exponential band model. Evaluates vertical profiles of optical quantities required for multiple scattering calculation. |
| MAPMS | Mapping routine, line of sight to vertical path. |
| CXDTA | Locates coefficient for double exponential. |
| C4DTA | Returns N$_2$ continuum absorption coefficient at required wavenumber. |
| ABCDTA | Moves double exponential coefficients into new arrays. |
| SLF296 | Loads self-broadened water vapor continuum at 296° K. |
| SLF260 | Loads self-broadened water vapor continuum at 260° K. |
| FRN296 | Loads foreign-broadened water vapor continuum at 296° K. |
| SINT | Performs interpolation for water vapor continuum. |
| C6DTA | Returns Rayleigh molecular scattering attenuation coefficient at required wavenumber. |
| C8DTA | Returns Chappuis ozone visible absorption coefficient at required wavenumber (13000 to 24200 cm$^{-1}$) |
| HNO3 | Determines nitric acid absorption coefficient at required wavenumber. |
| AEREXT | Interpolates aerosol attenuation coefficients and asymmetry parameter to required wavenumber. |
| GAMFOG | Computes attenuation of equivalent liquid water content in clouds. |
| INDX | Calculates real and imaginary part of refractive index of water. |
| DEBYE | Calculates wavenumber dependence of dielectric constant of water. |
| DOP | Calculates the real part of the dielectric constant for water. |
| AB | Calculates the imaginary part of the dielectric constant for water. |
| HERTDA | UV O$_2$ Herzberg continuum - analytic function. |
| SCHRUN | UV O$_2$ Schumann-Runge band model parameters. |
| O3HHT0 | UV O$_3$ Hartley band temperature dependent coefficient: constant term (24370 to 40800 cm$^{-1}$). |
| O3INT | Interpolation for Hartley band. |
| O3HHT1 | UVO$_3$ Hartley band temperature dependent coefficient: linear term. |
| O3INT | Interpolation for Hartley band. |
| O3HHT2 | UV O$_3$ Hartley band temperture dependent coefficient: quadratic term. |
| O3INT | Interpolation for Hartley band. |
| O3UV | UV O$_3$ interpolation for 40800-54054 cm$^{-1}$ region. |
| O2CONT | O$_2$ continuum for 1395-1760 cm$^{-1}$ region. |

TABLE 5-continued

| | Description of TRANS Subroutines |
|---|---|
| O2INT | Interpolation for $O_2$ continuum. |
| TNRAIN | Calculates extinction due to rain as a function of rain rate. |
| GMRAIN | Computes attenuation of condensed water in the form of rain. |
| RNSCAT | Calculates extinction, scattering and asymmetry parameter due to rain in microwave region. |
| DBLTX | Transmittacne from new double exponential band model. |
| SSRAD | Performs the layer by layer single scattering radiance sum. |
| PHASEF | Chooses correct phase function based on relative humidity, frequency, scattering angle, and model. |
| INTERP | Performs linear or logarithmic interpolation. |
| PF | Returns the appropriate phase function from the stored database. |
| HENGNS | Calculates phase function using Henyey-Greenstein method. |
| MSRAD | Sets up profiles of optical properties for vertical path. Evaluates path integral of source function, multiple scattered radiance contribution. |
| SOURCE | Contains solar intensity data and calculates lunar intensity. |
| FLXADD | Calculates upward and downward fluxes. Multiple scattered source function is evaluated from fluxes using the stream approximation. |
| SOURCE | Calculates solar intensity data and calculates lunar intensity. |
| SUN | Evaluates extraterrestrial solar irradiances. |

TABLE 6

| | Description of Block Data Subroutines |
|---|---|
| MLATMB | Model atmospheric data. Six stored atmospheric models. |
| TITLE | Titles for output. |
| PRFDTA | Aerosol profile data. |
| EXTDTA | Aerosol and cloud extinction, absorption and asymmetry parameters. |
| SF296 | Self-broadened absorption coefficients for water vapor continuum at 296° K. |
| SF260 | Self-broadened absorption coefficients for water vapor continuum at 260° K. |
| BFH20 | Foreign-broadened absorption coefficients for water vapor continuum at 296° K. |
| C4D | Nitrogen continuum absorption coefficients and visible ozone absorption coefficients. |
| MARDTA | Navy marine aerosol extinction and absorption data. |
| PHSDTA | 70 averaged phase functions and truth table identifying correct phase function. |
| MDTA | Cloud and rain modeled atmospheric data. |
| DSTDTA | Desert aerosol extinction, absorption coefficients and asymmetry parameters for 4 wind speeds. |
| ATMCOM | Initializes constants used in program. |
| ABCD | Stores the absorber model parameter for each gas for the double exponential formulation and the coefficients of each gas for the k-distribution. |
| BO3HHO | Contains $O_3$ Hartley/Huggins cross sections for 273K: constant term. |
| BO3HH1 | $O_3$ Hartley/Huggins cross sections: linear term. |
| BO3HH2 | $O_3$ Hartley/Huggins cross sections: quadratic term. |
| O3UVFD | $O_3$ UV absorption coefficients (40800 to 54054 $cm^{-1}$ |
| BO2C | $O_2$ continuum equivalent coefficients (1395–1760 $cm^{-1}$) |
| CPTRCG | Band model absorption coefficients for trace gases. |
| CPUMIX | Band model absorption coefficients for uniformly mixed gases. |
| CPH20 | Band model absorption coefficients for water vapor. |
| CPO3 | Band model absorption coefficients for ozone. |
| WVBNRG | Specification for wave number band region limits for each gas absorber. |
| SHUMG | Schumann - Runge $O_2$ band model. |
| SOLAR | Extraterrestrial solar spectral irradiances. |

As mentioned above, the software and instructions for the LOWTRAN 7 package are available from:
National Climatic Data Center, NOAA,
Environmental Data Services,
Federal Building,
Asheville, N.C. 28801,
(704) 259-0272.

The disclosure of this commercially-available information is specifically incorporated by reference into this patent, since the LOWTRAN 7 source code has approximately 19,000 lines of code. When printed out at 60 lines per page, it would be over three hundred and fifteen pages in length. This source code is useable with any system which uses a FORTRAN 77 compiler, and is immediately applicable to such systems which currently are using LOWTRAN 5, such as that of the above-cited Hoyler patent.

Figure 7:
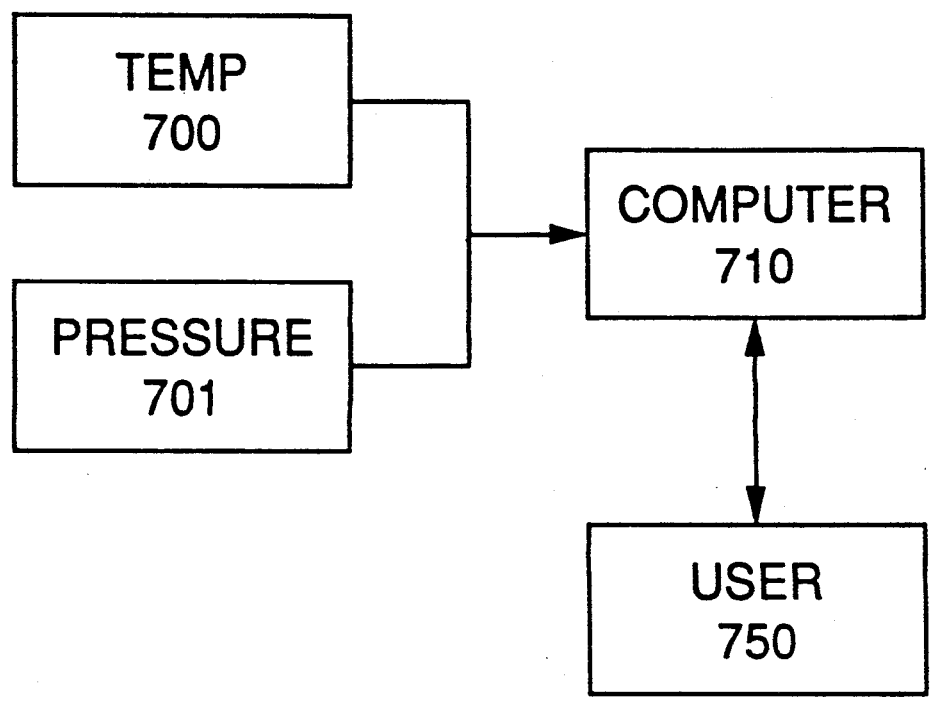
FIG. 7 is a block diagram of the elements of the apparatus of the present invention.

The reader's attention is now directed towards FIG. 7, which is a block diagram of a sensor system which uses the present invention. The system of FIG. 7 includes: a plurality of external sensors 700 and 701; a computer 710, and a host system 750 which is making use of the present invention.

As mentioned above, the system program will read user supplied atmospheric profiles when Model=0 or Model=7 is selected. Therefore, the external sensors 700 and 701 can be conventional sensors which detect atmospheric conditions including temperature, pressure and density as a function of altitude in proximity with the host system.

The computer 710 can be any conventional system which includes a FORTRAN 77 compiler, and which is electrically connected with the external sensors 700 and 701 along with the host system 750. As discussed above, the computer 710 produces an estimate of: atmospheric transmittance; atmospheric background radiance; single and scattered solar and lunar radiance, direct solar irradiance; and multiple scattered solar and thermal radiance for slant angles used by the host system 750. As mentioned above, when the computer 710 is loaded with LOWTRAN 7, it can make these calculations using an atmospheric data base which includes molecular profiles for thirteen minor and trace gases, and six reference atmospheres which define atmospheric temperature, pressure and density as a function of altitude.

The user block 750 in FIG. 7 can be any sensor system (such as that of the Holyer patent) or communication system which transmits signals through the atmosphere. Such systems can greatly benefit from the use of LOWTRAN 7. When they input their projected slant angles into the computer 710, they receive in return the estimates of atmospheric transmittance and background radiance, which affect such transmitted signals by different amounts. Phased array radar systems that attempt to track remote orbiting objects and determine their radar cross sections can benefit by such estimates when they are aware of the effect of the atmosphere on target echo return signals.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A low resolution atmospheric propagation model comprising:

a host system which transmits signals through at atmosphere along selected slant angles;

a first means for calculating atmospheric transmittance and atmospheric background radiance which is electrically connected with said host system, said first calculating means receiving said slant angles from said host system and determining therefrom an estimate of atmospheric transmittance and atmospheric background radiance for said slant angles with a 20 cm$^{-1}$ spectral resolution that can range between 0 and 50,000 cm$^{-1}$ in steps of 5 cm$^{-1}$;

a second means for calculating single scattered solar and lunar radiance for said atmospheric radiance, said second calculating means being electronically connected with said host system;

a third means for calculating direct solar irradiance for said atmosphere, said third calculating means being electrically connected with said host system; and a fourth means for calculating multiple scattered solar and thermal radiance for said atmosphere, said fourth calculating means being electrically connected with said host system.

2. A low resolution atmospheric propagation model, as defined in claim 1, which further comprises:

a computer memory which contains a plurality of reference atmospheres which each define atmospheric temperature, pressure and density as a function of altitude so that said first means for calculating atmospheric transmittance and atmospheric background radiance may function with and without external sensors which provide measured values of temperature, pressure and density.

3. A low resolution atmospheric propagation model, as defined in claim 2, wherein said computer memory includes an atmospheric data base which has separate molecular profiles for a plurality of minor and trace gases for altitudes that range between zero and one hundred kilometers, said minor and trace gases including: $H_2O$, $O_3$, $N_2O$, $CH_4$, $CO$, $O_2$, $CO_2$, $NO$, $NO_2$, $NH_3$, $HNO_3$ and $SO_2$.

4. A low resolution atmospheric propagation model as defined in claim 3, wherein said computer memory has molecular extinction and scattering equations along with atmospheric radiative transfer equations stored therein.

5. A low resolution atmospheric propagation model, as defined in claim 4, wherein said computer memory has aerosol, rain and cloud models along with atmospheric scattering models and solar data stored therein.

6. A low resolution atmospheric propagation model as defined in claim 5, wherein said computer memory has $O_2$ and $O_3$ ultra violet absorption characteristics for the model atmospheres stored therein.

7. A low resolution atmospheric propagation model, as defined in claim 6, wherein said computer memory has a water vapor continuum and molecular extinction and scattering models for the model atmospheres stored therein.

8. A low resolution atmospheric propagation model which comprises:

a host system which transmits signals through an atmosphere along selected slant angles;

a first means for calculating which calculates atmospheric transmittance and atmospheric background radiance and which is electrically connected with said host system, said first calculating means receiving said slant angles from said host system and determining therefrom an estimate of atmospheric transmittance and atmospheric background radiance for said slant angles with a 20 cm$^{-1}$ spectral resolution that can range between 0 and 50,000 cm$^{-1}$ in steps of 5 cm$^{-1}$;

a second means for calculating which calculates single scattered solar and lunar radiance for said atmospheric radiance, said second calculating means being electrically connected with said host system; and a computer memory which contains a plurality of reference atmospheres which each define atmospheric temperature, pressure and density as a function of altitude so that said first means for calculating atmospheric transmittance and atmospheric background radiance may function without external sensors which provide measured values of temperature, pressure and density.

9. A low resolution atmospheric propagation model, as defined in claim 8, wherein said computer memory includes an atmospheric data base which has separate molecular profiles for a plurality of minor and trace gases for altitudes that range between zero and one hundred kilometers, said minor and trace gases including: $H_2O$ $O_3$, $N_2O$, $CH_4$, $CO$, $O_2$, $CO_2$, $NO$, $NO_2$, $NH_3$, $HNO_3$ and $SO_2$.

10. A low resolution atmospheric propagation model as defined in claim 9, wherein said computer memory has molecular extinction and scattering equations along with atmospheric radiative transfer equations stored therein.

11. A low resolution atmospheric propagation model, as defined in claim 10, which further comprises:

a third means for calculating direct solar irradiance for said atmosphere, said third calculating means being electrically connected with said host system; and a fourth means for calculating multiple scattered solar and thermal radiance for said atmosphere, said fourth calculating means being electrically connected with said host system.

12. A low resolution atmospheric propagation model, as defined in claim 11, which includes:

a third means for calculating direct solar irradiance for said atmosphere, said third calculating means being electrically connected with said host system.

13. A low resolution atmospheric propagation model, as defined in claim 12, wherein said computer memory has aerosol, rain and cloud models along with atmospheric scattering models and solar data stored therein.

14. A low resolution atmospheric propagation model, as defined in claim 13, wherein said computer memory has $O_2$ and $O_3$ ultra violet absorbtion characteristics for the model atmospheres stored therein.

15. A low resolution atmospheric propagation model, as defined in claim 13 wherein said computer memory has a water vapor continuum and molecular extinction and scattering models for the model atmospheres stored therein.

16. A low resolution atmospheric propagation model comprising:
- a host system which transmits signals through an atmosphere along selected slant angles;
- a first means for calculating which calculates atmospheric transmittance and atmospheric background radiance and which is electrically connected with said host system, said first calculating means receiving said slant angles from said host system and determining therefrom an estimate of atmospheric transmittance and atmospheric background radiance for said slant angles with a 20 $cm^{-1}$ spectral resolution that can range between 0 and 50,000 $cm^{-1}$ in steps of 5 $cm^{-1}$;
- a second means for calculating which calculates single scattered solar and lunar radiance for said atmospheric radiance, said second calculating means being electrically connected with said host system; and
- a plurality of reference atmospheres which each define atmospheric temperature, pressure and density as a function of altitude so that said first means for calculating atmospheric transmittance and atmospheric background radiance may function without external sensors which provide measured values of temperature, pressure and density.

17. A low resolution atmospheric propagation model, as defined in claim 16, wherein said computer memory includes an atmospheric data base which has separate molecular profiles for a plurality of minor and trace gases for altitudes that range between zero and one hundred kilometers, said minor and trace gases including: $H_2O$, $O_3$, $N_2O$, $CH_4$, $O_2$, $NO$, $NO_2$, $NH_3$, $HNO_3$ and $SO_2$.

* * * * *